United States Patent
Fitz et al.

(10) Patent No.: US 6,852,350 B2
(45) Date of Patent: Feb. 8, 2005

(54) FLAVOR PRECURSORS

(76) Inventors: Wolfgang Fitz, Middenweg 285-I, NL-1098 AS Amsterdam (NL); Arnold Bruijnje, Nieuwe Bussummerweg 119, NL-1272 CG Huizen (NL); Sylvia Natalie Noomen, Groenhovenweg 93, NL-2803 DB Gouda (NL); Andrew Gerard Lynch, De Geldersman 9, NL-1274 HH Huizen (NL)

( * ) Notice: Subject to any disclaimer, the term of this patent is extended or adjusted under 35 U.S.C. 154(b) by 437 days.

(21) Appl. No.: 09/899,825

(22) Filed: Jul. 6, 2001

(65) Prior Publication Data

US 2002/0037349 A1 Mar. 28, 2002

(30) Foreign Application Priority Data

Jul. 7, 2000 (EP) .............................................. 00202431

(51) Int. Cl.$^7$ ................................................. A23K 1/22
(52) U.S. Cl. ....................... 426/535; 426/533; 426/534; 426/650
(58) Field of Search ................................. 426/533, 534, 426/535, 650

(56) References Cited

U.S. PATENT DOCUMENTS 3,787,473 A * 1/1974 van der Heijden et al. . 558/248
3,976,802 A 8/1976 Winter et al.
3,978,240 A * 8/1976 van der Heijden et al. . 426/535

FOREIGN PATENT DOCUMENTS

EP 0 167 376 A2 1/1988
GB 1379019 * 1/1975

OTHER PUBLICATIONS

Schutte, et al., Synthetic Precursors of Flavor Compounds with a Thiol Group, J. Agr. Food Chem., vol. 21, No. 2, pp. 226–229.*

* cited by examiner

*Primary Examiner*—Leslie Wong
(74) *Attorney, Agent, or Firm*—Fitch, Even, Tabin & Flannery

(57) ABSTRACT

The invention relates to flavor precursors represented by the formula $R_1$—S—CO—O—$R_2$ wherein $R_1$ is a specified heterocyclic radical, and the oxygen atom of the $R_2$—O— moiety is attached to a primary carbon atom of $R_2$; and to a foodstuff provided with such a flavor precursor.

15 Claims, No Drawings

FLAVOR PRECURSORS

The invention relates to flavour precursors, to foodstuffs containing one or more of such flavour precursors, to a process for flavouring foodstuffs by converting the flavour precursors into the actual flavour compounds as well as to the use of the flavour precursors in the manufacture of foodstuffs and of foodstuff flavours.

BACKGROUND OF THE INVENTION

There is a constant need for the enhancement and/or improvement of the flavour of foodstuffs. Many relevant foodstuffs flavour compounds, like furfurylthiol are very unstable, i.e. will deteriorate rather quickly under the foodstuff preparing, storing and consuming conditions, resulting in an undesirable low and/or short flavour impression of the foodstuff to be consumed.

In this respect it is brought to the fore that sulphur flavour precursors are known in the art. For instance, U.S. Pat. No. 3,978,240 already issued in 1976, relates to thiol precursors having the general formula $R_1$—S—CO—O—$R_2$, wherein $R_1$ is a substituted or unsubstituted alkyl, homo or heterocyclic radical having up to 10 carbon atoms and not more than two hetero atoms selected from the group consisting of oxygen and sulphur, and wherein $R_2$ represents a secondary or tertiary hydrocarbyl group containing 3–20 carbon atoms, attached to the oxygen with the secondary or tertiary carbon atom. However, no indication whatsoever is given in said U.S. Pat. No. 3,978,240 about the possible use of primary hydrocarbyl groups as examples for the meaning of $R_2$. Apparently, the inventors of U.S. Pat. No. 3,978,240 even intentionally excluded such primary hydrocarbyl groups for R2.

DESCRIPTION OF THE INVENTION

Surprisingly it has been found that a specific group of flavour precursors having the formula

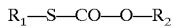

wherein $R_1$ is a heterocyclic radical selected from the group consisting of

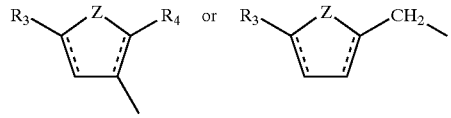

wherein Z is an oxygen or a sulphur atom, $R_3$ and $R_4$ represent hydrogen or an $C_1$-$C_4$ alkyl group and the symbol === represents a single or double bond, and $R_2$ is derived from a group of primary alcohol compounds consisting of $C_1$-$C_{18}$ alkanols, glycerol and mono-, oligo- and polysaccharides, wherein the oxygen of the $R_2$—O— moiety is attached to a primary carbon atom of $R_2$ do have excellent properties in enhancing and imparting flavour to foodstuffs like coffee at the moment the foodstuff is prepared and/or consumed.

The invention therefore relates to flavour precursors having the formula

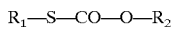

wherein $R_1$ and $R_2$ have the abovementioned meanings as defined in claim 1.

DETAILED DESCRIPTION OF THE INVENTION

The flavour precursors according to the invention are characteristic for the following thiol or mercapto- compounds from which the diester precursors can be prepared by one of the synthetic routes described below, the compounds are 4-mercapto-5-methyl-tetrahydrofuran-3-one
4-mercapto-2,5-dimethyl-tetrahydrofuran-3-one
3-mercapto-2-methyl-tetrahydrofuran (cis and trans)
3-mercapto-5-methyl-tetrahydrofuran (cis and trans)
3-mercapto-5-methyl-tetrahydrothiophene (cis and trans)
3-mercapto-2,5-dimethyl-tetrahydrothiophene
3-mercapto-2-ethyl-5-methyl-tetrahydrothiophene
4-mercapto-5-methyl-2,3-dihydrothiophene-3-one
4-mercapto-2,5-dimethyl-2,3-dihydrofuran-3-one
3-mercapto-2-methyl-4,5-dihydrofuran
3-mercapto-2,5-dimethyl-4,5-dihydrofuran
3-mercapto-2-methyl-2,3-dihydrothiophene
3-mercapto-2,5-dimethyl-2,3-dihydrothiophene
3-mercapto-2,5-dimethyl-2,3-dihydrofuran
3-mercapto-5-ethyl-2,3-dihydrothiophene
3-mercapto-2,5-dimethylfuran
3-mercapto-2-methylfuran
3-mercapto-5-methylfuran
3-mercapto-2-ethylfuran
2-mercapto-3,4-dimethylthiophene furfurylthiol
5-methylfurfurylthiol Further, the invention relates to foodstuffs provided with one or more flavour precursors, generally present in an amount of 0.0001–100 ppm, preferably 0.001–20 ppm.

A further aspect of the invention embraces the process for the flavouring of foodstuffs, i.e. enhancing or imparting the flavour by converting the flavour precursors in the foodstuffs at elevated temperature, for instance above 50° C., preferably 70–150° C., most preferably 90–130° C. under normal or elevated pressure in an aqueous medium. During said conversion of the precursors the desired flavour compounds and in principle harmless by-products are released. It is most likely that the conversion can be illustrated by the following equation:

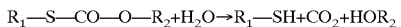

wherein $R_1SH$ represents the flavour compound, and $R_2OH$ an alcohol.

The precursor compounds according to the invention can be prepared by methods known in the art. Two generally applicable methods are:

(1) the conversion of chloroformic acid ester of the flavouring thiols with the formula $R_1$—S—COCl with the alcohols $HOR_2$ in the presence of a base; or (2) the conversion of the compound $R_1X$, wherein X represents a suitable halogen atom with an S-alkali metal salt of the thiocarbonic acid monoester of the alcohol $HOR_2$.

The foods in which the precursors (latent flavouring agents) have been incorporated are preferably to be heated before they are ready for consumption. Foodstuffs according to the invention in which a flavour precursor has been incorporated are, for instance, dry, canned and frozen soups, ready meals, croquettes, sauce cubes, bouillon cubes, baking fats, margarine, bread, cakes, products simulating meat, as texturised vegetable protein, sterilised beverages such as sterilised coffee beverages, and instant drinks which are prepared with hot water, such as instant coffee.

The esters can be incorporated in the foodstuffs as such or dissolved or dispersed in a carrier, such as a fat, or enrobed with maltose-dextrin, gelatin, gum arabic. They can be mixed with the food ingredients ready to be prepared or mixed with one of the ingredients.

The flavour precursors incorporated in foodstuffs according to the invention may be used in conjunction with other substances useful for the required purpose. Thus it is possible to use coffee flavour precursors in conjunction with substances like milk products, both fresh milk, treated fresh milk and milk powder, sugar products like granulated sugar, sodium bicarbonate, emulsifiers like sucrose esters, stabilising salts, antioxidants, hydrocolloids and coffee flavours per se.

Experimental

The invention will be illustrated by means of the following examples but should not be restricted thereto.

EXAMPLE 1

Preparation of O-ethyl S-(2-furylmethyl) thiocarbonate, (FFT-CO-OEt)

Furfurylthiol (527 g, 4.6 mol) and triethylamine (511 g, 5 mol) were added during a period of 6 hours at a temperature of 3–10° C. to a solution of ethyl chloroformate (546 g, 5 mol) in methyl tert-butyl ether (MTBE) (2000 ml). The resulting mixture was stirred overnight and allowed to reach room temperature. Water (700 g) was added to the mixture to dissolve the triethylammonium chloride, which was formed during the reaction. Concentrated hydrochloric acid (70 g) was added to neutralise the excess triethylamine (TEAM). The organic layer was separated and washed with a saturated sodium hydrogencarbonate solution (1000 g) and water (1300 g). The organic layer was dried over magnesium sulphate and filtered. After evaporation of the solvent the crude product was distilled at 130–132° C. at 30 torr to give 702 g (82%) O-ethyl S-(2-furylmethyl)thiocarbonate. The purity of the obtained product was determined by GC to be >99% and the structure confirmed by NMR spectroscopy.

Reaction scheme:

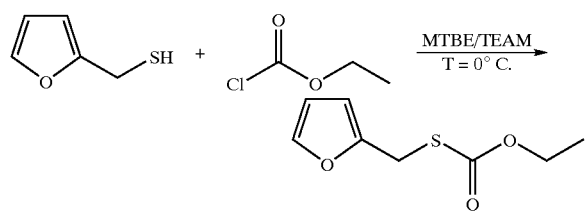

EXAMPLE 2

For the preparation of a sterilised coffee beverage the following procedure is followed:

1)
  (a) Weigh out 45 g of coffee blend into a stainless steel container.
  (b) Add 25 g of water at 98° C. to "steam the beans". Mix well and allow to stand for two minutes.
  (c) Add 450 g of deionised water (at 95° C.) to the coffee blend, hold for 5 minutes with gentle stirring every 1.5 minutes (cover the container with aluminium foil).
  (d) Pour the coffee solution into the "Kalita Coffee Filter" ensuring that all the coffee beans are added.
  (e) Collect the coffee extract and rinse the coffee beans in the filter three times with 60 g of deionised water at 95° C.
  (f) Add 50 g of granulated sugar to the coffee solution with stirring.
2) Add 0.8 g of $NaHCO_3$ to 50 g of deionised water at 90° C. and stir until dissolved;
3) Add the $NaHCO_3$ solution to the coffee extract obtained above.
4) Slowly add 50 g of the mill ingredient to the coffee extract with gentle stirring.
5) Add 0.1 g of the coffee flavour *⁾ (2% solution) as well as 0.01 ppm of the coffee flavour precursor obtained in Example 1, i.e. O-ethyl S-(2-furylmethyl)thiocarbonate and add water to bring solution to a mass of 1000 g.
6) Homogenise the solution with one pass through the Rannie homogeniser at 175 bar.
7) Cover the coffee beverage and heat it to 85° C. Fill it into cans and seal the cans.
8) Sterilise the cans at 121° C. for 20 minutes.
*) The composition of the coffee flavour is as follows:

| Flavour ingredient | Relative proportion |
|---|---|
| 3,5-Dimethyl-2-ethylpyrazine | 0.1 |
| Acetylpyrzine | 0.1 |
| 2,5-Dimethylpyrazine | 0.2 |
| 3-Methylbutanal | 0.6 |
| Guaiacol | 2 |
| Cyclotene | 4 |
| Dimethylcyclopentanedion | 2 |
| Diacetyl | 3 |
| Acetylpropionyl | 3 |
| Ethylmethylpyrazine | 4 |
| 2-Methoxy-4-vinylphenol | 2 |
| Butyric acid | 10 |
| Vanillin | 4 |
| Ethanol | rest |
| Total | 1000 |

A trained panel consisting of eleven evaluators compared the coffee sample prepared as described above to a coffee sample where no precursor was added. Eight out of the eleven evaluators preferred the coffee sample prepared as described above, as it showed an enhanced fresh coffee impression.

EXAMPLE 3

The following procedure is followed for the preparation of an instant coffee beverage:
1) A coffee extract was prepared in the same manner as defined in stage 1 of Example 2.
2) 0.01 ppm of the O-ethlyl S-(2-furylmethyl) thiocarbonate was added to the coffee extract.
3) Subsequently, the coffee extract obtained under step 2 was spray dried to give an instant coffee powder.
4) Finally a coffee drink was prepared by adding 1000 g of boiling water to 0.1 g of the instant coffee powder mixed well.

A trained panel consisting of eleven evaluators compared the coffee sample prepared as described above to coffee sample where no precursor was added. Nine out of the eleven evaluators preferred the coffee sample prepared as described above, as it showed a fresh roasted coffee impression.

EXAMPLE 4

Preparation of O-ethyl S-(2-methyl-3-furyl) thiocarbonate

To a mixture of ethyl chloroformate (0.96 g, 8.9 mmol) and 2-methylfuran-3-thiol (1 g, 8.7 mmol) in methyl ethyl ketone (15 ml) was added triethylamine (0.89 g, 8.9 mmol). The mixture was cooled in ice and stirred for 3 hours. After reaching room temperature water (10 g) was added to the mixture to dissolve the triethylammonium chloride formed during the reaction. Concentrated hydrochloric acid (2 g) was added to neutralise the excess triethylamine. The organic layer was separated and washed with a saturated sodium hydrogen carbonate solution (10 g), water (10 g) and finally a sodium sulphate solution (10 g). After evaporation of the solvent the residue was analysed by NMR spectroscopy and confirmed as O-ethyl S-(2-methyl-3-furyl) thiocarbonate, yield 86% (1.4 g, 7,5 mmol), purity 95%.

Reaction scheme:

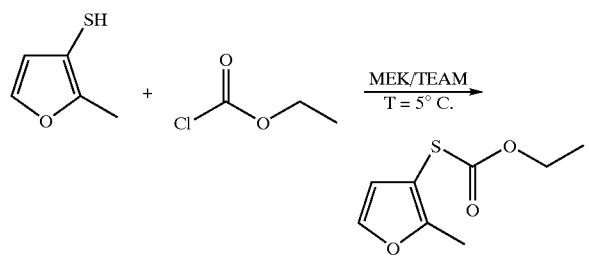

EXAMPLE 5

For the preparation of a bouillon the following procedure was followed:
1) To a standard bouillon substitute was added 0.05 ppm of O-ethyl S-(2-methyl-3-furyl) thiocarbonate obtained according to the process defined in Example 4.
2) The bouillon was then heated to 120° C. over 9 minutes, kept at 120° C. for 5 minutes then force cooled to room temperature over 30 minutes.

A trained panel consisting of eleven evaluators compared the retorted O-ethyl S-(2-methyl-3-furyl) thiocarbonate bouillon sample prepared as described above to a retorted 2-methylfuran-3-thiol bouillon. Nine out of the eleven evaluators preferred the retorted O-ethyl S-(2-methyl-3-furyl)thiocarbonate bouillon prepared as described above to the retorted 2-methylfuran-3-thiol bouillon, as it had a stronger beef profile.

EXAMPLE 6

For the preparation of a bread the following procedure was followed:

A bread dough containing flour 2500 g, water (8° C.) 1450 g, yeast 80 g, salt 50 g, ascorbic acid 0.1 g, Biobake 5000 0.25 g, Biobake 910 0.20 g, sodium stearyl lactilate 2012 6.25 g, shortening 25 g, and soy (enzyme activated) 7.5 g plus 0.5 g of a 0.1% solution of O-ethyl S-(2-methyl-3-furyl)thiocarbonate in medium-chain triglycerides (MCT) was made. The dough was kneaded using a Kemper 300/900 with dough temperature of 28° C. The bread was proved for 5 minutes (25° C.; 60% RH), divided by hand 5×780 g, made-up by hand, proved for a second time for 15 min (32° C.; 85% RH), made-up Op't Root (rolls 9.6; belt 4.5, 5) and proved for a final time for 60 min. (38° C.; 90% RH) The bread was baked for 25 minutes at 230/260° C.

A trained panel consisting of ten evaluators compared the of O-ethyl S-(2-methyl-3-furyl)thiocarbonate bread prepared as described above to 2-methylfuran-3-thiol bread. Eight out of the ten evaluators preferred the O-ethyl S-(2-methyl-3-furyl)thiocarbonate bread prepared as described above to the 2-methylfuran-3-thiol bread, as it had retained more flavour.

EXAMPLE 7

Preparation of O-ethyl S-(2,5-dimethyl-3-furyl) thiocarbonate

To a mixture of ethyl chloroformate (0.86 g, 7.9 mmol) and 2,5-dimethyl-furan-3-thiol (1 g, 7.8 mmol) in methyl ethyl ketone (10 ml) was added triethylamine (0.8 g, 7.9 mmol). The mixture was cooled in ice and stirred for 3 hours. After reaching room temperature water (10 g) was added to the mixture to dissolve the triethylammonium chloride which was formed during the reaction. Concentrated hydrochloric acid (2 g) was added to neutralise the excess triethylamine. The organic layer was separated and washed with a saturated sodium hydrogen carbonate solution (10 g), water (10 g) and finally a sodium sulphate solution (10 g). After evaporation of the solvent the residue was analysed and confined by NMR spectroscopy as O-ethyl S-(2,5-dimethyl-3-furyl) thiocarbonate yield 89% (1.4 g, 7 mmol) purity 91%.

Reaction scheme:

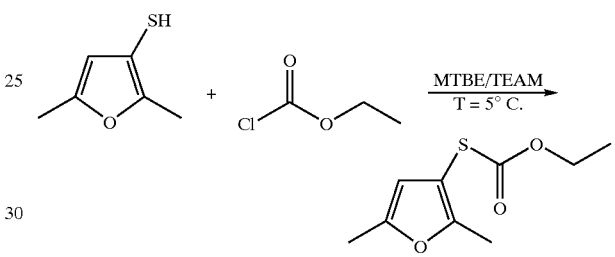

EXAMPLE 8

For the preparation of a chicken soup the following procedure was followed:
1) To a standard bouillon was added 0.05 ppm of O-ethyl S-(2,5-dimethyl-3-furyl) thiocarbonate.
2) The bouillon was then heated to 120° C. over 9 minutes, kept at 120° C. for 5 minutes then force cooled to room temperature over 30 minutes.

A trained panel consisting of eleven evaluators compared the retorted O-ethyl S-(2,5-dimethyl-3-furyl) thiocarbonate bouillon prepared as described above to a retorted 2,5-dimethyl-furan-3-thiol bouillon. Seven out of the eleven evaluators preferred the retorted O-ethyl S-(2,5-dimethyl-3-furyl) thiocarbonate bouillon prepared as described above to the retorted 2,5-dimethyl-furan-3-thiol bouillon, as it had a better chicken profile.

EXAMPLE 9

For the preparation of a bread the following procedure was followed:

A bread dough containing flour 2500 g, water (8° C.) 1450 g, yeast 80 g, salt 50 g, ascorbic acid 0.1 g, Biobake 5000 0.25 g, Biobake 910 0.20 g, sodium stearyl lactilate 2012 6.25 g, shortening 25 g, and soy (enzyme activated) 7.5 g plus 0.5 g of a 0.1% solution of O-ethyl S-(2,5-dimethyl-3-furyl) thiocarbonate in medium-chain triglycerides (MCT) was made. The dough was kneaded using a Kemper 300/900 with dough temperature of 28° C. The bread was proved for 5 minutes (25° C.; 60% RH), divided by hand 5×780 g, made-up by hand, proved for a second time for 15 min (32° C.; 85% RH), made-up Op't Root (rolls 9, 6; belt 4.5, 5) and proved for a final time for 60 min. (38° C.; 90% RH). The bread was baked for 25 minutes at 230/260° C.

A trained panel consisting of ten evaluators compared the of O-ethyl S-(2,5-dimethyl-3-furyl) thiocarbonate bread prepared as described above to 2,5-dimethyl-furan-3-thiol bread. Seven out of the ten evaluators preferred of O-ethyl S-(2,5-dimethyl-3-furyl) thiocarbonate bread prepared as described above to the 2,5-dimethyl-furan-3-thiol bread, as it had retained more flavour during the baking process.

EXAMPLE 10

Preparation of O-ethyl S-(3,4-dimethylthien-2-yl) thiocarbonate

To a mixture of ethyl chloroformate (0.96 g, 8.9 mmol) and 3,4-dimethylthiophene-2-thiol (1 g, 6.9 mmol) in methyl ethyl ketone (15 ml) was added triethylamine (0.76 g, 7.0 mmol). The mixture was cooled in ice and stirred for 3 hours. After reaching room temperature water (10 g) was added to the mixture to dissolve the triethylammonium chloride formed during the reaction. Concentrated hydrochloric acid (2 g) was added to neutralise the excess triethylamine. The organic layer was separated and washed with a saturated sodium hydrogen carbonate solution (10 g), water (10 g) and finally a sodium sulphate solution (10 g). After evaporation of the solvent the residue was analysed by NMR spectroscopy and confirmed O-ethyl S-(3,4-dimethylthien-2-yl)thiocarbonate, yield 79% (1.2 g, 5.5 mmol), purity 90%.

Reaction scheme:

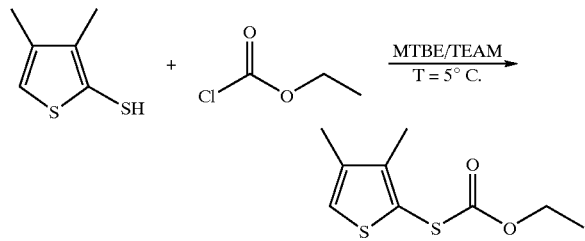

EXAMPLE 11

For the preparation of an onion soup the following procedure was followed:
1) To a standard onion soup was added 0.05 ppm O-ethyl S-(3,4-dimethylthien-2-yl) thiocarbonate.
2) The soup was then heated to 120° C. over 9 minutes, kept at 120° C. for 5 minutes then force cooled to room temperature over 30 minutes.

A trained panel consisting of ten evaluators compared O-ethyl S-(3,4-dimethylthien-2-yl) thiocarbonate soup prepared as described above to a retorted 3,4-dimethylthiophene-2-thiol soup. Eight out of the ten evaluators preferred the retorted O-ethyl S-(3,4-dimethylthien-2yl) thiocarbonate soup prepared as described above to the retorted 3,4-dimethylthiophene-2-thiol soup, as it had a better onion profile.

What is claimed is:

1. A flavor precuror represented by the formula:

$$R_1\text{—S—CO—O—}R_2$$

wherein $R_1$ is a heterocyclic radical selected from the group consisting of

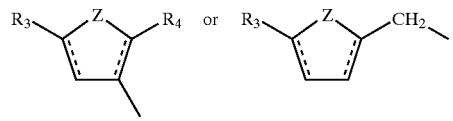

wherein Z is an oxygen or a sulphur atom, $R_3$ and $R_4$ represent hydrogen or an $C_1$–$C_4$ alkyl group and the symbol 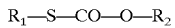

represents a single or double bond, $R_2$ is derived from a group of primary alcohol compounds consisting of $C_1$–$C_{18}$ alkanols, glycerol and mono-, oligo- and polysaccharides, wherein the oxygen of the $R_2$—O— moiety is attached to a primary carbon atom of $R_2$; and subjecting the foodstuff to elevated temperature in an aqueous medium such that a flavour compound is formed from the flavour precursor.

2. Flavor precursor according to claim 1, wherein the precursor is selected from the group consisting of O-ethyl-S-(2-furylmethyl)thiocarbonate, O-ethyl-S-(2-methyl-3-furyl)thiocarbonate and O-ethyl-S-(2,5-dimethyl-3-furyl) thiocarbonate.

3. Flavor precusor according to claim 2, wherein the precursor is O-ethyl-S-(2-furylmethyl)thiocarbonate.

4. Flavor precursor according to claim 2, wherein the precursor is O-ethyl-S-(2-methyl-3-furyl)thiocarbonate.

5. Flavor precursor according to claim 2, wherein the precursor is O-ethyl-S-(2,5-dimethyl-3-furyl)thiocarbonate.

6. A foodstuff containing a flavour precursor according to claim 1 or 2.

7. A foodstuff according to claim 6, wherein the foodstuff contains 0.0001 to 100 ppm of the flavour precursor.

8. A foodstuff according to claim 6, wherein the foodstuff contains 0.00 1 to 20 ppm of the flavor precursor.

9. A process for flavouring a foodstuff comprising providing a foodstuff incorporating a flavour precursor represented by the formula $$R_1\text{—S—CO—O—}R_2$$

wherein $R_1$ is a heterocyclic radical selected from the group consisting of

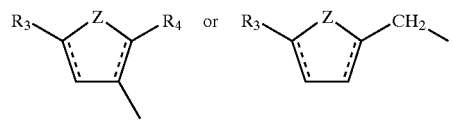

wherein Z is an oxygen or a sulphur atom, $R_3$ and $R_4$ represent hydrogen or an $C_1$–$C_4$ alkyl group and the symbol 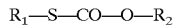

represents a single or double bond, $R_2$ is derived from a group of primary alcohol compounds consisting of $C_1$–$C_{18}$ alkanols, glycerol and mono-, oligo- and polysaccharides, wherein the oxygen of the R2—O— moiety is attached to a primary carbon atom of R2; and subjecting the foodstuff to elevated temperature in an aqueous medium such that a flavour compound is formed from the flavour precursor.

10. A process according to claim 9, wherein said elevated temperature is from 70° C. to 150° C.

11. A process according to claim 9, wherein the foodstuff incorporates 0.0001–100 ppm, of the flavour precursor.

12. A process according to claim 11, wherein the foodstuff incorporates 0.001 to 20 ppm of the flavor precursor.

13. A process according to claim 9, wherein the flavour precursor is selected from the group consisting of O-ethyl-S-(2-furylmethyl)thiocarbonate, O-ethyl-S-(2-methyl-3-furyl)thiocarbonate and O-ethyl-S-(2,5-dimethyl-3-furyl)thiocarbonate.

14. A process for preparing a foodstuff containing a flavour precursor, which comprises combining a foodstuff and a flavour precursor represented by the formula

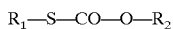

wherein $R_1$ is a heterocyclic radical selected from the group consisting of

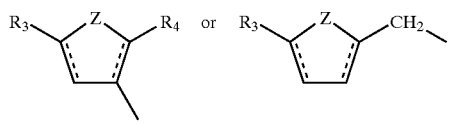

wherein Z is an oxygen or a sulphur atom $R_3$ and $R_4$ represent hydrogen or an $C_1$–$C_4$ alkyl group and the symbol ≡ represents a single or double bond, and $R_2$ is derived from a group of primary alcohol compounds consisting of $C_1$–$C_{18}$ alkanols, glycerol and mono-, oligo- and polysaccharides, wherein the oxygen of the $R_2$—O— moiety is attached to a primary carbon atom of $R_2$.

15. A process for producing a flavour compound which comprises converting a flavour precursor according to claim 1 or 2 to the flavour compound.

* * * * *